United States Patent [19]

Regan

[11] Patent Number: 4,795,458

[45] Date of Patent: Jan. 3, 1989

[54] STENT FOR USE FOLLOWING BALLOON ANGIOPLASTY

[76] Inventor: Barrie F. Regan, 2260 Redington Rd., Hillsborough, Calif. 94010

[21] Appl. No.: 69,364

[22] Filed: Jul. 2, 1987

[51] Int. Cl.⁴ .............................. A61F 2/06; A61F 2/04
[52] U.S. Cl. .......................................... 623/1; 623/12; 128/343; 427/2
[58] Field of Search ............... 623/1, 12, 66; 128/341, 128/343, 745, 324 R, DIG. 22, 303 R; 604/272, 273, 274; 427/2

[56] References Cited

U.S. PATENT DOCUMENTS

| | | | |
|---|---|---|---|
| 3,927,422 | 12/1975 | Sawyer | 623/341 X |
| 4,373,218 | 2/1983 | Schachar | 350/331 R |
| 4,503,569 | 3/1985 | Dotter | 128/34.3 X |
| 4,512,338 | 4/1985 | Balko et al. | 128/341 X |

Primary Examiner—Richard J. Apley
Assistant Examiner—Alan W. Cannon
Attorney, Agent, or Firm—Limbach, Limbach & Sutton

[57] ABSTRACT

A stent for implanting in a blood vessel following balloon angioplasty to prevent restenosis. The stent is a helical coil of a shape memory alloy tape or wire. The coil has a diameter less than that of the blood vessel in which it is to be implanted. The tape or wire has previously been wound to form a helical coil having a diameter equal to or slightly greater than the inside diameter of said blood vessel, this coil is than heated to an elevated temperature for a time sufficient to fix the shape of the second mentioned coil in the memory of the tape or wire, cooled to ambient temperature and then rewound to form the first mentioned helical coil.

5 Claims, 1 Drawing Sheet

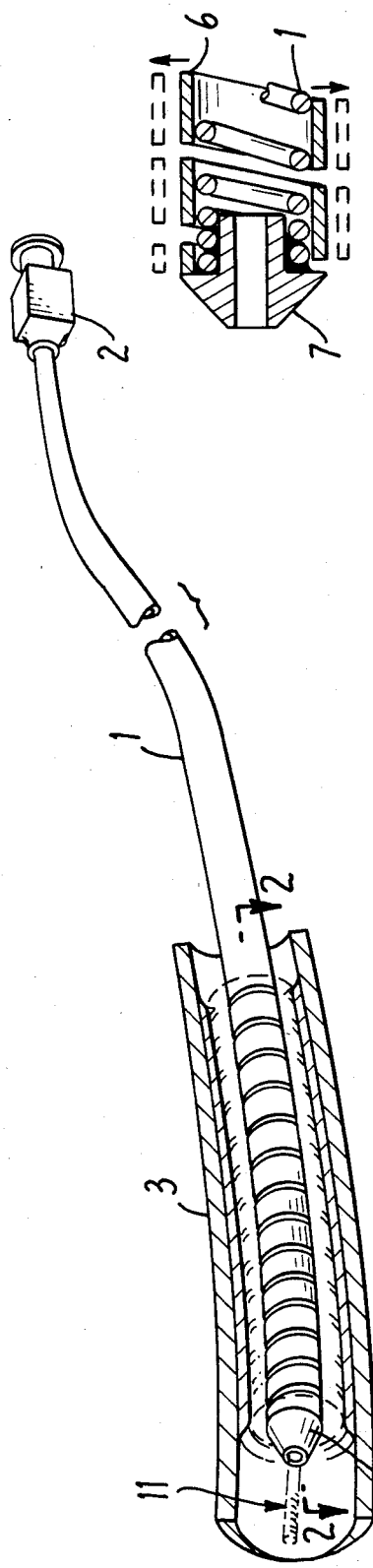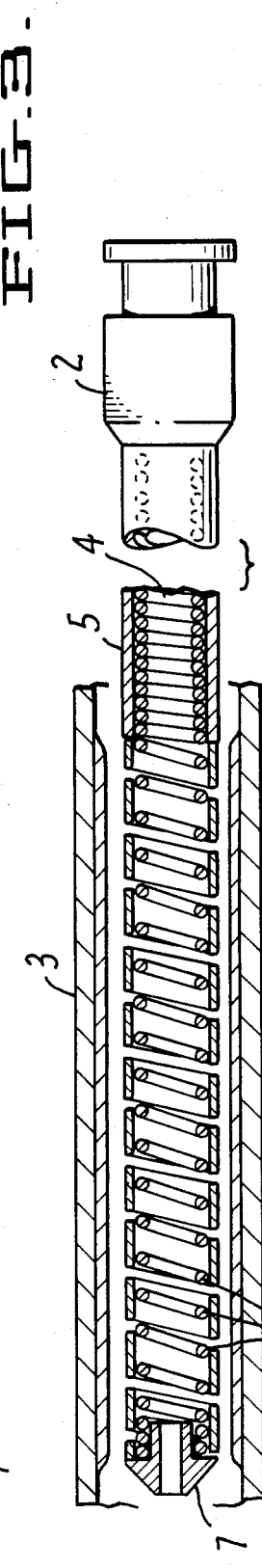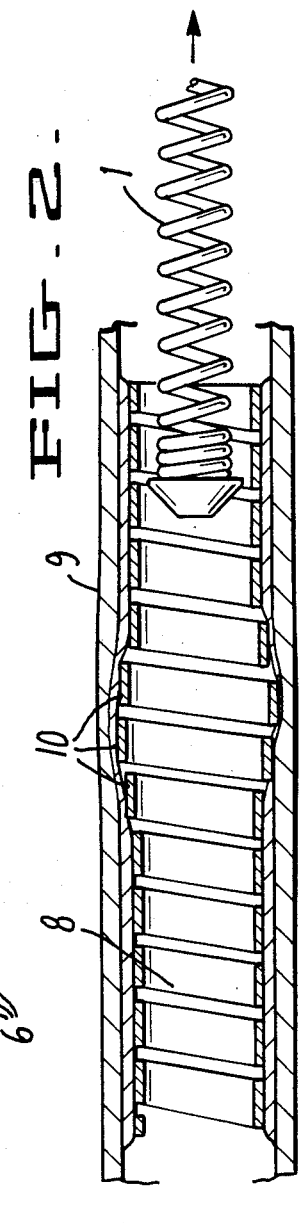

STENT FOR USE FOLLOWING BALLOON ANGIOPLASTY

Development of the balloon angioplasty technique began about ten years ago. The purpose of this technique is to open arteries in which the flow of blood has been impeded by build-up of arteriosclerotic plaques on the interior walls of the arteries. The technique consists in inserting a small diameter catheter into a blocked artery, the catheter has a small flexible balloon attached at its distal end. The catheter is moved thru the artery until the balloon is placed in the area of the artery in which blood flow is impeded by plaque build-up. The balloon is then inflated and flattens the plaque against the artery walls opening the artery to permit improved blood flow. The balloon is then deflated and removed leaving the plaque flattened against the artery walls.

After passage of several months time a proportion of the treated arteries, approximating one third, undergo restenosis, a reclosing of the artery at the treated area, requiring repetition of balloon angioplasty. The restenosis problem has received considerable attention and proposals have been made to deal with it.

BACKGROUND OF THE INVENTION

The most promising approach to restenosis prevention is the placement of a stent in the blood vessel which has undergone balloon angioplasty at the position in the vessel where the balloon was inflated immediately following removal of the balloon. The term stent is now in common use to denote a short tube, open at both ends for insertion in a blood vessel following balloon angioplasty to prevent restenosis, terms other than stent such as graft prosthesis, arterial endoprothesis, intraluminal graft and intravascular mechanical support may be and are frequently used instead of "stent" to convey the same meaning.

Dotter U.S. Pat. No. 4,503,569 for Transluminally Placed Expandable Graft Prosthesis describes a stent in detail. A Dotter et al. paper titled Transluminally Expendable Coil Stent Grafting was published in Radiology 147:25960 a month after his patent application was filed. Paper and patent are directed to the same subject matter. It is of passing interest that a Cragg et al. paper titled Nonsurgical Placement of Arterial Endoprotheses: A New Technique Using Nitinol Wire was published in Radiology 147:261-263 and is essentially identical in content with the Dotter et al. paper.

Both papers and the patent describe the making of a stent from nitinol, a shape memory alloy of titanium and nickel. The stent is a short helical coil of nitinol wire. The diameter of the helical coil is equal to or slightly greater than that of the blood vessel in which it is intended to use the stent. After the helical coil is made it is heated to fix the shape of the coil in the memory of the nitinol. The wire of the helical coil is then wound to form a helical coil having an appreciably smaller diameter than that of the first helical coil. The smaller diameter coil is then placed in the blood vessel at the place where the balloon was inflated. After placement in the blood vessel the coil is heated by passing warm (115°-125° F.) saline solution thru a catheter to heat the stent. Upon being heated the metal of the stent returns to its first larger diameter shape and presses firmly against the blood vessel walls where it is left to hold the blood vessel open preventing restenosis.

The term "nitinol" as used in the prior art, e.g. Dotter and Cragg, is not used to identify an alloy of fully specified composition, but rather to a "nitinol family" of alloys, all the members of which consist principally of nickel and titanium in varying proportions and many of which contain minor amounts of another element or elements to vary the properties of the alloy.

Shape memory alloys, also called "marmem" alloys, are materials which if used to form an article of particular shape which article is heated to elevated temperature, e.g. 500° C., and held at the elevated temperature for a short time period, e.g. 30 minutes, and then cooled at least to ambient temperature, retains a "memory" of the particular shape. If the article is them deformed or reshaped the memory of the particular shape remains with it and if the reshaped article is heated to a moderately elevated temperature, e.g. 90°-140° F., the reshaped article returns to the original particular shape. The moderately elevated temperature range at which the article returns to its original shape is called the Transition Temperature Range of the particular alloy. Both Dotter et al. and Cragg et al. used this property of nitinol to advantage.

Both Dotter et al. and Cragg et al., in their papers expressed the opinion that nitinol in addition to its shape memory which facilitated fixing a nitinol stent at a position in the blood vessel was resistant to formations of thrombi on its surface. Cragg et al. summarized their view saying, "By using Nitinol wire, the two main problems associated with this technique, namely, thrombosis of the endoprothesis and difficulty in introducing a graft of suitable size through conventional angiographic catheters, appear to be solved."

Since the publication of the Cragg et al. and Dotter et al. papers in April 1983 further experience with nitinol prostheses has shown that thrombus formation does occur on the surface of nitinol stents planted in the arteries. ( Wright et al. Radiology 1985; 156:69-72).

DESCRIPTION OF THE INVENTION

As a result of further work it has now been found that nitinol alloys and other marmem alloys can be treated to make them non-thrombogenic. It was observed that nitinol has a potential of +0.4 volts in the electromotive series of metals. There has been speculation in the literature that the potential of metals in the electromotive series might be a factor in thrombus formation but there has been no demonstration that potential of metals in the electromotive series is indeed a factor in thrombus formation.

It was conceived that the high potential of nitinol was considerably higher than human body potential and that if the potential could be reduced to near-body potential thrombosis might be prevented. Pursuit of this line of thought led to the idea of covering the nitinol surface with a thin layer of tin which has a potential of +0.14. These surfaces of a nitinol stent were covered with a tin coating about 0.0001 to 0.0002 inch in thickness.

Coated stents were implanted in the arteries of human patients immediately following balloon angioplasty. Blood flow through the implanted stents was monitored by x-ray, pressure gradient and Doppler evaluations. No indication of thrombus formation has been observed.

The treated stents are prepared by winding a length of wire or tape of a marmem alloy around a mandrel having a diameter equal to or slightly greater than that of the blood vessel in which it is to be implanted to form a helix, then heating the helix to an elevated temperature for a time to impress the shape of the helix on the memory of the alloy, then removing the helix from the mandrel and covering the surface of the helix with a thin coating of tin, then inserting a second mandrel having a smaller diameter than that of the first used mandrel into the helix and twisting the helix to bring its coils into close contact with the smaller mandrel and then removing the helix from the mandrel.

The tin coating may be laid down on the alloy by any conventional method, electroplating, sputtering, vacuum evaporation and the like. The tin coating may be covered with a very thin coating of indium about 100 to 1000 Angstrom units in thickness preferably by electroplating and the stent is then heated to a temperature near the indium melting point for example to a temperature of 150° C. for a time sufficient to cause diffusion of indium into the tin coating increasing its resistance to corrosion. The indium content of the tin coating after diffusion of the indium into the tin layer is about 1% to 10% by weight.

The stent as above described must be transported through the blood vessel which has undergone balloon angioplasty to the point in the vessel where the balloon expansion had occurred and there heated to its transition temperature to expand it and bring it into firm contact with the vessel walls. For this purpose an insertion catheter is employed.

The beveled tip has a hole passing through it to communicate with the interior of catheter 1. The hole in the beveled tip is sized to fit over the guide wire 11 of the conventional guide catheter. Catheter 1 is guided by guide wire 11 as it is pushed through guide catheter 3 to the desired position.

The insertion catheter will be described with reference to the appended drawings in which FIG. 1 is a schematic drawing showing the catheter with stent attached.

FIG. 2 is a cross section of the distal end of the catheter with the stent attached.

FIG. 3 is a cross section of the distal end and tip of the catheter.

FIG. 4 is a cross section of the modified form of the stent disposed in the blood vessel and the catheter being withdrawn.

Referring to FIG. 1 of the drawings the catheter 1 is shown extending from Luer Lok Hub 2 to the distal end of the catheter, the final two inches being shown in enlarged cross section and being free of the polyvinyl chloride with which the remaining length of the catheter is covered. Beveled tip 7 is fixed to the distal end of catheter 1.

FIG. 2 shows the distal end of the catheter lying inside a conventional guide catheter 3 through which a balloon catheter was passed during balloon angioplasty. The balloon catheter was moved through the guide catheter until the balloon portion of that catheter passed into the plaque covered portion of the blood vessel walls prior to inflation of the balloon and the guide catheter was left in the blood vessel after withdrawal of the balloon catheter for use during the stent implantation. The drawing except for Luer Lok Hub 2 shows only the terminal inches of the catheter which may be of considerably length eg. 55 inches. Stainless steel helix 4 which is about 0.05 inches in diameter is close wound with normal tension so that the coils are touching and for all its length except for the final few inches are coated with polyvinyl chloride 5. Typically the wound stainless steel wire is 0.008 inches in diameter. In the last one to three inches of the helix the coils are not closely wound but are spaced apart about equal to the wire diameter. This arrangement permits passage of hot saline solution through the close wound and plastic covered portion of the catheter to the catheter end to where the hot solution flows in between the spaced apart coils into the blood vessel to contact the stent and cause its expansion and contact with the blood vessel walls. Stent 6 is helically wound about stainless steel helix 4. The stent has a length usually from about 0.5 to 2.0 inches and an outside diameter less than that of the blood vessel in which it is placed. After heating the stent to its transitional temperature range its outside diameter becomes equal to or slightly greater than that of the blood vessel.

FIG. 3 shows the distal end of the catheter and the immediately adjacent coils of the catheter. Beveled tip 7 terminates the length of the catheter and is soldered to the final two or three coils of the catheter. The stent is held on helix 4 over which it is wound by a beveled tip 7 at its lower end and by the plastic layer surrounding the stainless steel helix at its upper end.

FIG. 4 shows stent 8 implanted in blood vessel 9 and catheter 1 being withdrawn from the blood vessel after delivery of the stent. The stent shown in FIG. 4 is a modified form which is not of uniform diameter throughout but which is outwardly bowed in its central area where several central coils 10 of the stent have larger diameters than the remaining coils. The purpose of this form of stent is to prevent spasm of the blood vessel which occasionally occurs when the full length of the stent which may be one to two inches is expanded to contact the blood vessel walls. In the stent of FIG. 4 only central coils 10 contact the blood vessel walls when the stent is heated to transition temperature range. These few coils engage the blood vessel walls and maintain the stent in fixed position in the blood vessel.

Stents, above described, have been implanted in eight patients. Several of the patients had health conditions which precluded recourse to heart surgery and the others had previously been through balloon angioplasty which was followed by restenosis or requested stent implantation instead of surgery. The Institutional Review Boards of the hospitals at which stent implantation was proposed reviewed the status of the patients and authorized implantation of the stents. All patients are alive and comfortable. The patients' conditions have been regularly checked by x-ray, pressure gradient measurement and Doppler evaluation and no evidence whatever of thrombus formation has been found.

Protheses other than stents, e.g. heart valves and vena cava filters have been implanted in the cardiovascular systems of human patients and have experienced thrombosis problems. Such prostheses have been formed from nitinol alloys and from stainless steel. There has been no evidence whatever of thrombus formation on the tin coated nitinol stents implanted in the eight patient in which these stents have been implanted. It is clear that the surface coating of tin prevents thrombus formation on the stent surfaces. A tin coating on prostheses made from corrosion resistant materials such as stainless steel will prevent or very significantly inhibit thrombosis.

I claim:

1. A stent for implanting in a blood vessel following balloon angioplasty to prevent restonosis, said stent consisting of a helical coil of marmem alloy tape or wire having a diameter less than that of the blood vessel in which it is to be implanted, said tape or wire having earlier been wound to form a helical coil having a diameter equal to or greater than the inside diameter of said blood vessel and heated to an elevated temperature for a time to fix the shape of the second mentioned helical coil in the memory of the alloy and then covered with a thin surface coating of tin.

2. The stent defined in claim 1 where in the marmem alloy is a nitinol.

3. The stent defined in claim 1 wherein the tin surface coating contains from about 1% to 10% by weight of indium.

4. A stent for insertion into a blood vessel following balloon angioplasty to prevent restenosis which comprises:

a helical coil having a diameter slightly less than the diameter of the blood vessel in to which it is to be inserted, said coil being formed of a corrosion resistant shape memory alloy having a transition temperature in the range about 39°-60° C. which has been wound into a helical coil having a diameter equal to or slightly greater than that of the said blood vessel, heated to an elevated temperature for a time sufficient to fix the larger diameter coil shape in the memory of said alloy, then coated with a thin surface coating of tin and then rewound to form the first mentioned helical coil.

5. The stent defined in claim 4 wherein the shape memory alloy is a nitinol.

* * * * *